United States Patent
Zikeli et al.

(10) Patent No.: US 7,314,570 B2
(45) Date of Patent: Jan. 1, 2008

(54) METHOD FOR REMOVING HEAVY METALS FROM MEDIA CONTAINING HEAVY METALS BY MEANS OF A LYOCELL MOULDED BODY, CELLULOSIC MOULDED BODY COMPRISING ABSORBED HEAVY METALS, AND THE USE OF THE SAME

(75) Inventors: Stefan Zikeli, Regau (AT); Thomas Endl, Vöcklabruck (AT)

(73) Assignee: Zimmer A.G., Frankfurt am Main (DE)

( * ) Notice: Subject to any disclaimer, the term of this patent is extended or adjusted under 35 U.S.C. 154(b) by 403 days.

(21) Appl. No.: 10/487,114

(22) PCT Filed: Nov. 29, 2001

(86) PCT No.: PCT/EP01/13970

§ 371 (c)(1),
(2), (4) Date: Aug. 2, 2004

(87) PCT Pub. No.: WO03/018166

PCT Pub. Date: Mar. 6, 2003

(65) Prior Publication Data

US 2005/0035057 A1 Feb. 17, 2005

(30) Foreign Application Priority Data

Aug. 20, 2001 (DE) ................. 101 40 772

(51) Int. Cl.
*C02F 3/00* (2006.01)
(52) U.S. Cl. ...................... 210/683; 210/688
(58) Field of Classification Search ........... 210/683, 210/688
See application file for complete search history.

(56) References Cited

U.S. PATENT DOCUMENTS

| 3,347,968 A | 10/1967 | Rainer et al. |
| 4,361,493 A | 11/1982 | Kiefer |
| 5,496,860 A | 3/1996 | Matsumoto et al. |
| 5,671,757 A | 9/1997 | Woodings |
| 5,792,399 A | 8/1998 | Meister et al. |
| 5,888,526 A * | 3/1999 | Tsubai et al. ........... 424/405 |
| 2003/0186611 A1 | 10/2003 | Zikeli et al. |

FOREIGN PATENT DOCUMENTS

| CS | 1295717 | 2/1970 |
| DE | 19747518 | 4/1999 |

(Continued)

OTHER PUBLICATIONS

International Search Report for Application No. PCT/EP 01/13970.

(Continued)

*Primary Examiner*—Chester T. Barry
(74) *Attorney, Agent, or Firm*—McDonnell Boehnen Hulbert & Berghoff LLP (57) ABSTRACT

The invention relates to a method for the adsorption of heavy metals from media containing heavy metals, using a Lyocell moulded body. The invention also relates to a cellulosic moulded body comprising adsorbed heavy metals and the use of the same as an antibacterial and/or fungicidal moulded body.

23 Claims, 1 Drawing Sheet

FOREIGN PATENT DOCUMENTS

| | | |
|---|---|---|
| DE | 19917614 | 10/2000 |
| EP | 0 860 522 | 8/1998 |
| EP | 0 860 522 A | 8/1998 |
| GB | 1101485 | 1/1968 |
| GB | 1295717 | 11/1972 |
| WO | WO 95/14398 | 6/1995 |
| WO | WO 00/46438 | 8/2000 |
| WO | WO 00/63470 | 10/2000 |

OTHER PUBLICATIONS

English Translation of PCT International Preliminary Examination Report for International Application No. PCT/EP2001/013970 filed Nov. 29, 2001.

* cited by examiner

FIG. 1

METHOD FOR REMOVING HEAVY METALS FROM MEDIA CONTAINING HEAVY METALS BY MEANS OF A LYOCELL MOULDED BODY, CELLULOSIC MOULDED BODY COMPRISING ABSORBED HEAVY METALS, AND THE USE OF THE SAME

The invention relates to a method for the adsorption of heavy metals from media containing heavy metals, using a Lyocell moulded body. The invention also relates to a cellulosic moulded body comprising adsorbed heavy metals and the use of the same as an antibacterial and/or fungicidal moulded body.

Methods for removing heavy metals from media containing heavy metals are known. In these methods, problems arise with diluted waste water or industrial process water flows, whereby the main cause behind these flows is the drag-out from process stages, often caused by rinsing operations.

In WO 89/00444, therefore, a method for separating nickel ions from aqueous solutions is described. For this purpose, the solution is subjected to liquid membrane permeation in a first stage and, in a second stage, the remaining nickel is removed using solvent extraction.

Although it is attempted to limit the amount of rinse water by using optimised rinsing concepts, useful materials and auxiliary agents are also carried along with the pollutants. What is required, therefore, is a closure of circuits for intra-plant material and water, whereby the waste waters that arise in the process should be further cleaned up.

In WO 00/63470, a method for manufacturing cellulosic moulded bodies with a high adsorbing capacity is described, whereby an ion exchanger is added to the cellulose fibre during its manufacture. The ion exchanger can have a polystyrene or polyacrylate basis, in particular acidic or alkaline derived styrene-divinylbenzene copolymer resins or acrylic acid-divinylbenzene copolymer resins. The moulded bodies obtained are suitable for eliminating the temporary hardness and heavy metals from water.

Furthermore, a method for recovering metals from alkaline metal solutions that contain ammonia is described in U.S. Pat. No. 4,500,396, whereby a weakly acidic material, capable of cation exchange, is used, where this material is a polymeric fibrous web with monomers containing carboxyl groups grafted onto it. The polymeric fibrous web can consist of nylon, cellulose, polyethylene or polytetraethylene fibres or mixtures of these.

Furthermore, a method for recovering copper is also described in U.S. Pat. No. 4,500,396. Carboxyl groups are grafted to felt made of polymer fibres by means of radiation. In this way, one obtains a cation exchanger, with which the copper can be filtered out of the waste waters.

The known methods have the disadvantage that, on the one hand, synthetic ion exchangers are added to the moulded bodies used in the process and these are therefore not biodegradable, and, on the other hand, the durability of the moulded bodies suffers from the addition of the ion exchangers. In addition, the manufacture of the moulded bodies requires effort, because these bodies must be modified with functional groups. Before use, the ion exchanger groups, such as carboxyl groups, require additional treatment with acid, lye or salts in order to activate the groups, as a result of which the method requires effort to carry out.

Furthermore, fibres, fibrous webs and sponges are known that contain a metal with an antibacterial effect.

Consequently, an antibacterial fibre is described in U.S. Pat. No. 5,496,860 that includes a fibre capable of ion exchange and a metal ion with an antibacterial effect, that is bonded via an ion exchange reaction. The fibres contain sulfonic acid groups or carboxyl groups as groups capable of ion exchange.

The known antibacterial fibres and methods described in the preceding have the manufacturing disadvantage that active groups, capable of ion exchange, are introduced after the normal fibre manufacturing process, and these then have to be activated with metal ions in a further step.

Furthermore, a stratiform antibacterial fibrous web is described in U.S. Pat. No. 5,652,049 that consists either of synthetic fibres with zeolites in which Zr or Ag ions are incorporated or of cellulose fibres with chitosan particles.

Furthermore, a body that is germicidal and that absorbs urine, faecal substances and blood is described in DE 31 35 410; this body contains a water-soluble copper salt that is not irritating or damaging to human skin, and which is concentrated in the surface that first comes into contact with the separation products. The material used for the manufacture of such bodies is a cellulose fibre fleece or wadding that consists of native cellulose (fluffed sheets). This native cellulose must be sprayed and treated in order to be able to adsorb a slight amount of pollutants.

Therefore, the adsorption of the antibacterial substances is poor and, in particular, the result is uneven absorbing of these substances, which consequently also results in an uneven release and effect of the antibacterial properties.

A further example of a method for the manufacture of antibacterial fibres is described in U.S. Pat. No. 5,458,906, whereby the fibres are immersed in a solution with monovalent copper ions and a solution with carbonate, borate and mixtures of the two. The fibres can be natural or synthetic fibres, such as acrylic fibres, grafted cotton, wool, linen or fibre mixtures.

These antibacterial fibres and methods for their manufacture have the disadvantage that the base product is a "finished" fabric or fibre, the absorbing of the active antibacterial substances takes place only on the surface, and the active substances are not uniformly and homogenously incorporated during the spinning process.

The object of the invention under consideration is therefore to solve the problems of the known methods and fibres described in the preceding. In particular, the object of the invention is to provide a simple, economical and reliable method for removing heavy metals from media containing heavy metals and a reliable antibacterial and/or fungicidal moulded body that is also easy to manufacture.

The solution of the object is a method for removing heavy metals from media containing heavy metals, whereby the medium containing heavy metals is brought into contact with a Lyocell moulded body.

A further solution is a cellulosic moulded body, whereby at least one heavy metal is adsorbed on it, as well as its use as an antibacterial and/or fungicidal material.

To be understood under the term "Lyocell moulded body" in the sense of this invention is a moulded body that is obtained in a known way by dissolving cellulose in an amine oxide hydrate, preferably N-methylmorpholine-N-oxide (NMMO) monohydrate, and introduction of the solution into a non-solvent for the cellulose, preferably water, by means of which the moulded body precipitates in the non-solvent. In this way, a Lyocell moulded body is obtained, whereby the cellulose that forms the moulded body is not modified with additional functional groups, in particular, sulfonic acid or carboxyl groups, i.e., it is unmodified cellulose. The cellulose forming the moulded body can contain customary additives, as well as other natural and/or synthetic polymers, as described in the following, and can also be subjected to customary aftertreatment processes.

It was a surprise to discover that the Lyocell moulded body manufactured in this way is excellently suitable for removing heavy metals from media containing heavy metals, because this body adsorbs a large amount of heavy metals without additional functional groups. It is assumed that the adsorption of the heavy metals takes place on the Lyocell moulded bodies via its free carbonyl, carboxy and/or hydroxyl groups.

The Lyocell moulded body can be present as a regenerated moulded body or in a modified incorporated form, and can be used in the method according to the invention as an ion exchanger, adsorption filter or filtering material, in order to remove the heavy metals contained in aqueous solutions or gases from the same.

Preferably, heavy metals selected from the group consisting of Ag, Cu, Zn, Hg, Sn, Cd, As, Pb, Sb, Zr, Ni, Fe, Au, Pd, Pt, Ir and mixtures of these in metallic, ionic or complexed form can be removed from the medium with the method according to the invention. Media containing heavy metals mainly arise in aqueous waste material, such as in metallurgical works or during metal recycling processes, and these waste materials are not permitted to be dumped without removing the substances contained in them that are damaging to the environment. A further application area for the method according to the invention is the recovery of valuable heavy metals from consumed solutions, such as solutions containing copper, which arise during the manufacture of semiconductor plates, and from photographic baths containing silver.

Further preferred application areas for the method for removing heavy metals according to the invention are:

Chemical Industry:
Treatment and recovery of waste water and process solutions for removing heavy metals, particularly during the manufacture and disposal of batteries and storage batteries;
Recycling of useful solutions, particularly removal of Hg and heavy metals of alkali chloride electrolysis brines;
Pd recovery in the mirror metallizing and battery industries;
Ag recovery in the semiconductor industry; and
Ag recovery from photographic developing baths.

Metal Extraction/Electroplating/Metal Surface Treatment:
Cycling of process solutions;
Waste water fine cleaning, particularly in the electroplating, chromatizing and semiconductor industries during degreasing, etching, galvanizing, anodic oxidation, hot-dip galvanizing, painting, etc.;
Recovery and thereby service life extension of baths, particularly in the electroplating, chromatizing and semiconductor industries.

Environmental Engineering:
Removal of heavy metals, such as mercury and chromate, from the groundwater;
Treatment of leachate from landfills to reduce the heavy metal content;
Removal of heavy metals and mercury from waste waters from flue gas purification in incineration plants, mainly household refuse incineration plants.

Using methods according to the invention, new concepts and procedural solutions can be realised. Consequently, by using conventional water technology, such as membrane processes (micro, ultra and nano filtration; reverse osmosis), liquid membrane permeation, electrolysis processes, crystallization, solvent extraction, activated carbon filters, circuits can be closed through the use of Lyocell moulded bodies according to the invention.

After the use of the Lyocell moulded body in the method according to the invention, useful materials, such as silver, copper or tungsten, can simply be fed back into the process by subjecting the Lyocell moulded body, such as filtering material, used according to the invention to incineration or acid treatment.

The method according to the invention can also be advantageously used for removing heavy metals from cigarette smoke, such as Cd, i.e., the Lyocell moulded body can be used as a filtering material in cigarettes. In particular, a Lyocell moulded body in the form of filtering material can be used as a cigarette filter.

By carrying out the method according to the invention, from roughly 1 to roughly 100 g/l of heavy metals, depending on the type of heavy metal, heavy metal concentration, temperature, detention time and liquid-to-solid ratio, i.e., the ratio of fibres to waste water, can be removed from the medium containing heavy metals.

In a further, especially preferred embodiment, a plant and/or animal material can additionally be added to the Lyocell moulded body used in the method according to the invention. The plant and/or animal material is preferably a material made of marine plants or marine animals.

The material of marine plants is preferably selected from the group consisting of algae, kelp, eel grass, particularly algae. Examples for algae include brown algae, green algae, red algae, blue algae or mixtures of these. Examples of brown algae are *Ascophyllum* spp., *Ascophyllum nodosum, Alaria esculenta, Fucus serratus, Fucus spiralis, Fucus vesiculosus, Laminaria saccharina, Laminaria hyberborea, Laminaria digitata, Laminaria echroleuca* and mixtures of these. Examples of red algae include *Asparagopsis armata, Chondrus cripus, Maerl beaches, Mastocarpus stellatus, Palmaria palmata* and mixtures of these. Examples of green algae are *Enteromorpha compressa, Ulva rigida* and mixtures of these. Examples for blue algae are *Dermocarpa, Nostoc, Hapalosiphon, Hormogoneae, Porchlorone*. Classification of the algae can be found in the textbook *Botanik für Hochschulen* E. Strasburger; F. Noll; H. Schenk; A. F. W. Schimper; 33rd edition, Gustav Fischer Verlag, Stuttgart-Jena-New York; 1991.

The material made of marine plants can be obtained in the known way.

First, the material made of marine plants is harvested. The harvested material can be further processed in a variety of ways. The material of marine plants can be dried at temperatures of up to 450° C. and can be reduced to small pieces using ultrasound, wet ball mills, pin mills or counter-rotating mills, by means of which a powder is obtained, which can optionally also be fed through a centrifugal stage for classification. A powder obtained in this way can already be added to a Lyocell moulded body that can be used according to the invention.

Furthermore, this powder made of a material of marine plants can in addition be subjected to an extraction process, for example, with steam, water or an alcohol, such as ethyl alcohol, as a result of which a liquid extract is obtained. This extract can also be used as an additive to the Lyocell moulded body that can be used according to the invention.

The harvested material of marine plants can also be subjected to a cryogenic process to reduce it to small pieces. In this process, it is reduced to small particles with a size of approximately 100 μm at −50° C. If required, the material obtained in this way can be further reduced to small pieces, whereby particles with a size of approximately 6 to approximately 10 μm are obtained.

The material from the outside shells of marine animals is preferably selected from oceanic sediments, shells of shrimp or bivalves, lobsters, crustaceans or prawn, reduced to small size, and/or coral.

In the case of oceanic sediments, the material from marine animal shells can be used directly. If material from the shells of shrimp or bivalves, lobsters, crustaceans and/or prawn is used, the material must be reduced to small pieces.

It is also possible to use a mixture of materials from marine plants and shells from marine animals, as well as the extracted products. The quantitative composition of material of marine plants and shells of marine animals is preferably 50% by weight to 50% by weight. Preferably, material from marine plants is used according to the invention.

It is furthermore possible to use particles of the material of marine plants and/or shells of marine animals in the particle size range from 200 to 400 μm, preferably 150 to 300 μm. Preferably, particles with small particle sizes, such as 1 to 100 μm, more preferably 1 to 5 μm, are also used. It is also possible to use uniform materials or different algae materials with mixed particle sizes An example for a usable material of marine plants is a powder of *Ascophyllum nodosum* with a particle size of 95%<40 my, which contains 5.7% protein by weight, 2.6% fat by weight, 7.0% fibrous components by weight, 10.7% moisture by weight, 15.4% ash by weight and 58.6% hydrocarbons by weight. Furthermore, it contains vitamins and trace elements, such as ascorbic acid, tocopherols, carotene, barium, niacin, vitamin K, riboflavin, nickel, vanadium, thiamine, folic acid, folinic acid, biotin and vitamin $B_{12}$. In addition, it contains amino acids, such as alanine, arginine, aspartic acid, glutamic acid, glycine, leucine, lysine, serine, threonine, tyrosine, valine and methionine.

The material of marine plants and/or shells of marine animals can be present in the Lyocell moulded body in an amount of 0.1 to 30% by weight, preferably 0.1 to 15% by weight, more preferably 1 to 8% by weight, particularly 1 to 4% by weight, relative to the weight of the Lyocell moulded body. In particular, if the Lyocell moulded body is in the form of a fibre, the amount of material of marine plants and/or shells of marine animals is preferably 0.1 to 15% by weight, particularly 1 to 5% by weight.

The continuous or discontinuous mixing of cellulose and the material of marine plants and/or shells of marine animals can be accomplished with devices and processes as described in WO 96/33221, U.S. Pat. No. 5,626,810 and WO 96/33934.

In the method according to the invention, the Lyocell moulded body is preferably used in the form of fibres, filaments, fibrous webs, foils, films, membranes, sausage casings, filter paper, particularly manufactured using short cut fibres 3-15 mm in combination with other materials like cellulose, and non-wovens.

In a preferred embodiment, the Lyocell process can be carried out by introducing the plant and/or animal material, as described in the following. To manufacture a workable mass, a solution of cellulose, NMMNO and water is manufactured by means of first forming a suspension of cellulose, NMMNO and water and then continuously transporting this suspension in a 1 to 20 mm thick layer under reduced pressure through a heat exchange surface by means of rotating elements. During this process, water is evaporated until a homogenous cellulose solution results. The amount of cellulose in the cellulose solutions obtained in this way can be from 2 to 30% by weight, the amount of NMMNO can be from 68 to 82% by weight, and the amount of water can be from 2 to 17% by weight. If required, additives, such as inorganic salts, inorganic oxides, finely dispersed organic substances or stabilizers, can be added to this solution.

Then the plant and/or animal material, particularly the material of marine plants and/or shells of marine animals, in the form of powder, powder suspension or in liquid form, as an extract or suspension, is continuously or discontinuously added to the cellulose solution obtained in this way.

Depending on the method, the plant and/or animal material, particularly the material of marine plants and/or shells of marine animals, can also be added after or during the continuous reduction of the dry cellulose to small pieces, for example, in the form of algae material in the original size, as a powder or highly concentrated powder suspension. The powder suspension can be produced in water or any other solvent in the concentration required and necessary for the method.

Furthermore, it is also possible to feed the material of marine plants and/or shells of marine animals to a mashing process with simultaneous reduction to small size. The mashing can be carried out either in water, in lye or also in the solvent that is needed for dissolving the cellulose later. In this case, as well, the material of marine plants and/or shells of marine animals can be added as a solid, powder or suspension, or also in liquid form.

The polymer composition enriched with the material of marine plants and/or shells of marine animals can, in the presence of a derivation agent and/or a solvent known for the dissolving process, be converted into a workable extrusion mass.

A further possibility for adding the material of marine plants and/or shells of marine animals is addition during a continuous dissolving process, such as described in EP 356419 and U.S. Pat. Nos. 5,049,690 and 5,330,567.

Alternatively, the addition can be carried out discontinuously while maintaining a master batch of the cellulose solution. Preferably, the material of marine plants and/or shells of marine animals are added continuously.

The material of marine plants and/or shells of marine animals can be added in any other stage of the moulded body's manufacturing process. For example, it can be fed into a pipeline system with the corresponding mixing by system-contained static mixing elements or stirring elements, such as known inline refiners or homogenizers, i.e., Ultra Turrax devices. If the method is carried out in continuous batch operation, e.g., using a stirred vessel cascade, the algae material, in solid, powder, suspension or liquid form, can be introduced at the position that is the most nearly optimal for the process. Dispersion can be achieved with known stirring elements that are coordinated to the method.

Depending on the particle size used, the formed, incorporated extrusion or spinning mass can be filtered before or after being incorporated. Conditional on the fineness of the product used, it is also possible to do without filtration in spinning processes with large nozzle diameters.

If the spinning masses are very sensitive, the material can be added in the suitable form through an injection point directly before the spinning nozzle or the extrusion tool.

A further possibility, if the algae material is present in a liquid form, is to add this material to the continuously spun thread during the spinning process.

The cellulose solution obtained in this way can be spun using a conventional process, such as dry-jet-wet, wet-spinning, melt blown process, centrifugal pot spinning, funnel spinning or dry spinning. The patent specifications U.S. Pat. Nos. 5,589,125 and 5,939,000, as well as EP 0574870 B1 and WO 98/07911 describe spinning processes for manufacturing cellulose fibres according to the NMMO method. Where necessary, the formed moulded bodies are subjected to the conventional aftertreatment processes for chemical fibres for filaments or staple fibres.

In addition to the spinning methods, there are also extrusion methods for manufacturing flat films, round films, casings (sausage casings) and membranes.

The use of a Lyocell moulded body that contains plant and/or animal material, particularly algae material, in the method according to the invention, as described in the preceding, has the additional advantage that, in the method according to the invention, the Lyocell moulded body is capable of exchanging Ca, Mg and Na ions and, furthermore, up to 50% more heavy metals can be bonded to it than when a pure Lyocell moulded body is used.

Therefore, in this embodiment, the method according to the invention is particularly suitable for treating media containing heavy metals in application areas as described in the preceding. Particularly when a Lyocell moulded body that contains material from marine plants is used, the method according to the invention has the advantage that heavy metals are absorbed across the entire cross-section of the Lyocell moulded body, like a fibre. In this way, a larger amount of heavy metals, referred to the weight of the moulded body, can be absorbed than when a cellulose moulded body with function groups is used.

A further solution of the object of the invention is a cellulosic moulded body with at least one adsorbed heavy metal on it, whereby the heavy metal can be present in the form of a metallic, ionic or complexed form.

The cellulosic moulded body is preferably selected from the group consisting of cellulose regenerated moulded bodies, such as carbamate, viscose and Lyocell moulded bodies, particularly preferred, a Lyocell moulded body.

The content of the heavy metals adsorbed on the cellulosic moulded body according to the invention is preferably at least roughly 1 mg/kg, preferred at least roughly 10 mg/kg, particularly preferred at least roughly 70 mg/kg, preferably at least roughly 200 mg/kg, more preferred at least roughly 500 mg/kg, particularly at least roughly 1000 mg/kg, referred to the total weight of the cellulosic moulded body.

Preferred is the heavy metal selected from the group consisting of Ag, Cu, Zn, Hg, Sn, Cd, As, Pb, Sb, Zr, Ni, Fe, Au, Pd, Pt, Ir and mixtures of these, particularly metals with germicidal effects such as Ag, Cu, Zn, Zr and mixtures of these. In particular, heavy metals with an antibacterial and/or fungicidal effect are used. The expression "heavy metal" in the sense of the invention includes metallic, ionic and complexed forms of the heavy metals. Ionic forms include salts and oxides of the heavy metals. A particularly preferred oxide is silver(I) oxide and a particularly preferred salt is silver nitrate. Further oxides that can be used are AgO as well as further Ag(I) and Ag(III) oxides, such as $Ag_2O_3$. Further salts that can be used are silver chloride, silver sulphide, silver proteins, silver carbonate, and the soluble silver salts silver acetate, silver sulphate, silver citrate, silver lactate and silver picrate.

In one embodiment of the cellulosic moulded body according to the invention, a plant and/or animal material is added to this body, as described in the preceding. In this way, the result is a very uniform distribution of the at least one heavy metal in the cellulosic moulded body according to the invention. This has the advantage that, on the one hand, a large amount of heavy metal can be introduced into the moulded body and, on the other hand, a very uniform release of the adsorbed heavy metal takes place.

The cellulosic moulded body according to the invention can also contain other natural and/or synthetic polymers in addition to cellulose, where these polymers can either be added to the spinning composition or can also be present in mixtures as bi-component and multi-component fibres in a side-by-side, island-in-the-sea or sheath-core configuration. Preferable is that the additional polymer is selected from the group consisting of polyester, polyamide, polyvinyl chloride, cellulose carbamate, cellulose acetate, cupro, viscose, polyacrylonitrile, polyolefin, Teflon, hemp, wool, linen and cotton.

The manufacture of the cellulosic moulded body according to the invention can be carried out by means of immersing the manufactured moulded body into an aqueous solution containing heavy metal, separating the aqueous solution containing heavy metal and optionally washing and drying the Lyocell moulded body obtained. The loading processes are carried out for between 1 minute and several hours, depending on the application area.

The cellulosic moulded body can remain in the aqueous solution containing heavy metal for up to roughly four hours. The aqueous solution containing heavy metal is preferably roughly 0.1 M in relation to the heavy metal contained in it.

A further possibility for manufacturing the cellulosic moulded body according to the invention, if a plant and/or animal material is incorporated in this body, is if first the plant and/or animal material, such as algae material reduced to small pieces and ground, is brought into contact with a heavy metal solution, such as a silver nitrate solution, and the mixture obtained in this way is then sprayed dry, whereby the grinding can take place dry or wet and under normal or high pressure. This material, endowed with heavy metal, can then be incorporated into the cellulosic moulded body according to the invention during the manufacture of this body. This material can, for example, be sprayed onto a fibrous web for textile, technical or medical use, together with the normally used bonding agent, or alone, during the manufacture of the fibrous web, before the fibrous web is dried and processed into the final product. The ground, spray-dried or damp algae material, loaded with heavy metal, can also be added to the spinning solution for the manufacture of the cellulosic moulded body.

The cellulosic moulded body according to the invention is particularly usable as an antibacterial and/or fungicidal material, particularly as an antibacterial fibre, antibacterial fibrous web, hygiene article, medical protective clothing, antibacterial water filter, non-woven, filter material or antibacterial sponge. A further possible use concerns the use as bandaging gauze for burn injuries.

The cellulosic moulded body according to the invention is particularly usable as a filtering material for liquid and gaseous media in which pollutants are contained, for example as a cigarette filter to remove heavy metals and other pollutants from the smoke. By using a cellulosic moulded body according to the invention, for example, in the form of modified fibres in a cigarette filter that was loaded with palladium and copper salts, toxic carbon monoxide can be converted into carbon dioxide, in addition to the removal of heavy metals from the smoke. This catalyst effect of copper and palladium salts in an aqueous solution, in order to oxidize carbon monoxide into carbon dioxide or sulphur dioxide into sulphur trioxide, is described in U.S. Pat. No. 3,790,662.

In particular, the following products can be manufactured from the cellulosic moulded bodies according to the invention:

If the Lyocell moulded body according to the invention is present in the form of fibres or filaments, yarns for weaving mills and knitting mills can be made for the manufacture of filtering materials on a fabric basis or for the manufacture of antibacterial fabrics that can be used for clothing and medical applications. Included in the yarns made of Lyocell fibres according to the invention that lie in the number range Nm1/1 to 170/1, are:

Condenser yarns, which include flat yarns and tweed yarns and that can either be manufactured purely of Lyocell or of different combinations with wool, cashmere, silk, mohair, alpaca, polyester, polyamide and/or viscose;

Worsted yarns, which include Siro, crepe and cordonnet yarns, that can either be manufactured purely of Lyocell or of different combinations with shear wool, cashmere, silk, mohair, alpaca, polyester, polyamide and/or viscose;

Ring spun yarns, carded or combed, that can either be manufactured purely of Lyocell or of different combinations with cotton, silk, linen, microfibres and/or viscose;

OE yarns, which can either be manufactured purely of Lyocell or of different combinations with cotton, wool, linen and/or viscose;

Fibre-effect yarns, which include boucle, terry, ondé twisted yarns, and that can either be manufactured purely of Lyocell or of different combinations with cotton, silk, polyester, polyamide and/or viscose;

Filament-effect yarns, which include sable, terry, shaded and slub yarns, and that can either be manufactured purely of Lyocell or of different combinations with polyester, polyamide, viscose and/or Trevira CS;

Filament yarns, flat, textured or high-twist, that can either be manufactured purely of Lyocell or of different combinations with acetate, triacetate, polyester, polyamide and/or viscose;

Technical yarns, which include, for example, Parafil Plyfil or Corespun, and that can either be manufactured purely of Lyocell or of different combinations with Kevlar, Preox, Nomex, Kermel, carbon, glass, steel, viscose and/or polyester; and Elastic yarns, which include, for example, wrap yarn, Siro, Plyfil or Corespun, and that can either be manufactured purely of Lyocell or of different combinations with cotton, shear wool, polyester, linen, elasthan and/or viscose.

The combinations with other fibres have the advantage that the product's wearing comfort and properties for hygienic applications and clothing can be adjusted using mixture components. The antibacterial properties or ion exchange properties are not impaired by this.

These yarns can be processed into fabrics using, for example, shuttle, rapier, projectile or jet machines, which, for example, are extremely well suited for the application areas of ion exchange and antibacterial properties. Likewise, the yarns can be processed into knitted fabrics using flat bed, single jersey, double knit and warp knit machines, which are likewise extremely well suited for the application areas of ion exchange and antibacterial properties.

Furthermore, the Lyocell moulded bodies according to the invention, optionally in the form of fibres/filaments, can be further processed into endless or cut form to non-woven products for industrial uses, such as roofing materials, separators, filters, reinforcing basic bodies, sealing materials and insulating materials, for special papers such as dust filters, filters for waste and/or process waters, sausage casings, for textile applications such as medical applications (swabs and gauze), wadding, stockings, shoe inserts, shoe inner lining, bedding, home textiles, serviettes, washing clothes, paper towels or nappies.

The fabrication can either be processed into pure Lyocell products or in combination with other fibres, with super absorbers, with activated carbon and with native cellulose (fluff cellulose) in order to achieve a combination effect.

Consequently, combinations with super absorbers display extremely high absorption of water; the combination with activated carbon in granulate or fibre form also shows, in addition to an antibacterial effect and an ion exchange effect, an extra capability of adsorbing organic materials and/or colouring substances.

It is also possible to add natural and synthetic bonding agents, such as latex polymers, diethylene, butadiene, vinyl acetate and/or styrenes to the cited bonded fabrics. These bonding agents are preferably added in an amount of from 1-30% by weight. Furthermore, thickeners, catalysts, filler materials, colouring substances, lubricants, optical bleaching agents and/or defoamers can be added.

The manufacture of the non-wovens or fibrous webs can take place using a carding, wetlaid, airlaid or extrusion process.

The fibrous webs manufactured in this way can be compacted by means of needlepunch, stitch bond, hydroentanglement, spun bond or melt blowing treatment. Additional possibilities are chemical compaction with a corresponding bonding agent or thermal compaction or the admixing of thermoplastic additives, which are compacted into a fibrous web with the cellulosic fibres.

In a finisher stage, the non-woven products can additionally be chemically and/or mechanically treated, in order, for example, to optimize moisture absorption and moisture transport, or to improve the absorption capability, fire resistance, electrical resistance, friction properties and/or abrasion properties.

Included in the mechanical aftertreatments are, among others, calendering, suede finishing, raising the nap, polishing, shearing and brushing or combing. Further aftertreatment techniques are lamination, embossing and profiling using a calender or creping.

The non-woven products can be constructed in one or more layers and present a typical mass per unit area from 15-500 $g/m^2$.

Furthermore, the cellulosic moulded bodies can find application in the form of antibacterial sponges or sponge wipes.

These can be obtained according to the continuous manufacture of viscose sponges described in U.S. Pat. No. 3,382,303. Cellulose xanthate is diluted with an aqueous solution, in which cellulose, reduced to small pieces, is dispersed as a reinforcing agent for the sponge to be formed. Crystals of sodium sulphate or sodium phosphate are then added to this paste. This paste is extruded in a form, open at the top, and fed through a precipitation bath at 95° C. for approximately 15 minutes. Final regeneration takes place in a second bath at 55-75° C. In the further sequence, the sponge is then washed, bleached, washed again and then dried. Before the drying, the sponge is squeezed in order to reduce the water content.

A moulded body, according to the invention and with antibacterial effect, is manufactured by adding a heavy metal, in metallic, ionic or complexed form, during an extra process step, for example either before or after the drying. Preferred embodiments can be derived from the following examples.

Furthermore, Lyocell sponges according to the invention can be obtained as described in WO 99/27835. In this process, a pore-forming agent and fibre reinforcement are mixed in with the N-oxide water cellulose solution and the mass is applied to a conveyor belt using sheeting dies. The sedimentation takes place in a warm spinning bath in order to liquefy and dissolve the pore-forming agent. One variant is application of the N-oxide water cellulose solution to a plastic net. No blowing agent is used, so that neither the mechanical stability nor a corresponding abrasion. resistance of the sponge or sponge wipe can be achieved. WO 99/27835 describes impregnation of the sponges with substances with a biocide effect, such as isothiazolon, benzimidazole derivatives, tertiary ammonia salts, zeolites, glycerine and propylene glycol.

A further method for manufacturing Lyocell sponges according to the invention is similarly described in WO 97/23552. In this process, a cellulose solution of an aqueous amine oxide is mixed with a pore-forming agent (an alkaline salt or alkaline earth salt or an inorganic acid, e.g., $Na_2SO_4$) and a blowing agent. Then the mass is subjected to conditions that lead to decomposition of the blowing agent and therefore to a foaming of the cellulose solution. The foamed cellulose solution is brought into contact with water in order to precipitate the cellulose and wash out the pore-forming agent.

A Lyocell sponge according to the invention, with an antibacterial effect, is manufactured by adding a heavy metal in metallic, ionic or complexed form, during an extra process step either before or after the drying. The detailed embodiment can be derived from the following examples.

Carbamate sponges according to the invention can be manufactured analogously to the method described in JP21172302, whereby again heavy metal is added at any stage of the process, preferably again before or after the sponge is dried.

In the following, the invention is explained by using examples.

EXAMPLE 1

3250 g NMMNO (60.5%), 331 g MoDo, DP 500, solid content 94%, 2.0 g propyl gallate (~0.63% referred to the cellulose content) as well as 40 g of the brown algae *Ascophyllum nodosum* (broken into small pieces) were mixed and the mixture obtained in this way was heated to 94° C. A discontinuously produced spinning solution with a cellulose content of 12%, a solids content of 13.4% and a viscosity of 5,264 Pa.s was obtained. The spinning solution obtained in this way was spun into fibres, whereby the following spinning conditions were maintained:

| | |
|---|---|
| Storage tank temperature = | 90° C. |
| Spin block temperature, nozzle = | 80° C. |
| Spinning bath = | 4° C. |
| Spinning bath concentration (start) = | 0% (distilled water) |
| Spinning bath concentration (end) = | 5% NMMNO |
| Spinning pump = | 0.6 cm³/r |
| Nozzle filter = | 19200 M/cm² |
| Spinning nozzle = | 500 hole 90 µm; Au/Pt |
| Final take-off = | 30 m/min |

The fibres were cut to a fibre staple of 40 mm, washed without solvent and given a 10 g/l softening (50% Leomin OR-50% Leomin WG (fatty acid polyglycol ester containing nitrogen, from the company Clariant GmbH)) at 45° C. or the fat overlay for improved further processing of the fibre was applied and dried at 105° C.

After the drying, fibre moisture of 11% was regulated. No additional bleaching process was carried out before the drying.

TABLE 1

| | | Example 1 Part 1 |
|---|---|---|
| Fineness, titre | [dtex] | 1.58 |
| FB tear strength, dry | [cN/tex] | 40.0 |
| FB tear strength, wet | [cN/tex] | 32.4 |
| FB tear strength, loop | [cN/tex] | 7.1 |
| Maximum tensile force elongation, dry | [%] | 10.7 |
| Maximum tensile force elongation, wet | [%] | 12.3 |
| Wet module | [cN/tex] | 225 |

Table 1 shows that the spinning characteristics of the spinning solution obtained according to this example were good.

EXAMPLE 2

Lyocell cellulose fibres were continuously manufactured according to Example 1, whereby the respective amount, the conditions of the continuously maintained process and the physical properties of the fibres obtained are listed in the following Table 2. 8% brown algae material, referred to the cellulose, was used.

Table 2 presents the fibre data for the modified Lyocell fibre.

TABLE 2

| | | Modified Lyocell fibre, manufactured continuously |
|---|---|---|
| Fineness, titre | [dtex] | 1.34 |
| FB tear strength, dry | [cN/tex] | 35.9 |
| FB tear strength, wet | [cN/tex] | 31.1 |
| FB tear strength, loop | [cN/tex] | 11.2 |
| Maximum tensile force elongation, dry | [%] | 11.9 |
| Maximum tensile force elongation, wet | [%] | 13.4 |
| Wet module | [cN/tex] | 210 |

EXAMPLE 3

Furthermore, Lyocell fibres were continuously manufactured according to Example 1, with the difference that no brown algae material was added.

The physical data of the fibres obtained are summarized in the following Table 3.

TABLE 3

| | | Lyocell fibre, manufactured continuously |
|---|---|---|
| Fineness, titre | [dtex] | 1.4 |
| FB tear strength, dry | [cN/tex] | 42.2 |
| FB tear strength, wet | [cN/tex] | 36.3 |
| FB tear strength, loop | [cN/tex] | 15.2 |
| Maximum tensile force elongation, dry | [%] | 15.5 |

TABLE 3-continued

|  |  | Lyocell fibre, manufactured continuously |
| --- | --- | --- |
| Maximum tensile force elongation, wet | [%] | 15.2 |
| Wet module | [cN/tex] | 202 |

The analysis of the fibres produced in Examples 2+3 with regard to their metal ion content can be derived from the following Table 4.

The metal ion content was determined according to the testing method:

1. Microwave decomposition and
2. Metal determination according to DIN EN ISO 11885 (E22)

TABLE 4

|  | Modified Lyocell fibre Example 2 - untreated | | Lyocell fibre Example 3 - untreated | |
| --- | --- | --- | --- | --- |
|  | [mg/kg fibre] | [mmol/kg fibre] | [mg/kg fibre] | [mmol/kg fibre] |
| Arsenic | <5 | <DL | <5 | <DL |
| Silver | <2 | <DL | <2 | <DL |
| Antimony | <5 | <DL | <5 | <DL |
| Tin | <5 | <DL | 6.1 | 0.05 |
| Cadmium | <1 | <DL | <1 | <DL |
| Copper | <5 | <DL | <5 | <DL |
| Lead | 5.4 | 0.03 | 5.5 | 0.03 |
| Zinc | <5 | <DL | <5 | <DL |
| Calcium | 115 | 2.87 | 38 | 0.95 |
| Magnesium | 112 | 4.61 | 95 | 3.91 |
| Sodium | 330 | 14.35 | 306 | 13.31 |
| Mercury | <1 | <DL | <1 | <DL |

DL = Detection Limit

From Table 4, it is apparent that, in particular, calcium, magnesium and sodium ions are contained in the fibres.

EXAMPLE 4

1 l of 0.05 M $AgNO_3$ solution was added to 30 g of the fibres produced according to Example 1 and shaken for four hours.

After this treatment, the fibre material was filtered by suction and washed with completely demineralised water until no more silver traces (test with a NaCl solution) were detected.

The fibres were dried in a circulating air drying cabinet at approximately 105° C.

The fibre obtained in this way was analysed for its silver content. For this purpose, to a portion of the fibre material 1N nitric acid (1 hour) was added in order to dissolve the silver. The nitric acid solution was filtered off and then titrated with 0.1 N NaCl. To improve the visibility of the end point of the titration, the filtrate was heated so that the resulting precipitate agglomerated.

30 g of the fibres produced in Example 3 were treated in the same way.

EXAMPLE 5

1 l of 0.1 M $CuSO_4$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 6

1 l of 0.1 M $ZnSO_4$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 7

1 l of 0.1 M $Hg(NO_3)_2$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 8

1 l of 0.1 M $SnCl_4$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 9

1 l of 0.1 M $CdSO_4$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 10

1 l of 0.1 M $AgNO_3$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 11

1 l of 0.1 M $As_2O_3$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 12

1 l of 0.1 M $Pb(NO_3)_2$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 13

1 l of 0.1 M $SbCl_5$ solution was added to 30 g of the fibres produced in Example 2 and shaken for four hours.

After this treatment, the fibre material was filtered by suction and washed with completely demineralised water. The fibres were dried in a circulating air drying cabinet at approximately 105° C.

30 g of the fibres produced in Example 3 were treated in the same way.

EXAMPLE 14

The maximum amount of the fibres produced according to Examples 4 to 13 that could be taken up on the respective metal ions was examined.

The results are summarized in the following Table 5.

What is surprising is that the Lyocell fibres present a high adsorption capacity, and that this adsorption capacity can be increased by another 50% with the modified Lyocell fibres.

EXAMPLE 15

The fibres produced according to Example 4 were then examined for bacterial resistance.

The determination was carried out following the Japanese Industrial Standard, JIS L1902:1998 Testing method for antibacterial of textiles. *Staphylococcus aureus*, as a gram-positive bacterial strain, and *Klebsiella pneumoniae*, as a gram-negative bacterial strain, were used.

The bacteria were furthermore applied to fibre material from Example 1 and, as a growth control, standard cotton was subjected to the same test treatment.

After 18 hours of incubation, the bacterial growth inhibiting or bacterial reduction activity is determined from the bacterial content (the number of colony-forming units—CFU) in the sample and the control.

To calculate this antibacterial activity, the difference in the base-10 logarithms of the number of colony forming units (CFU) in the control sample and the sample, each after 18 hours of incubation, is formed.

The classification is done in three classes—slight activity, significant activity and strong activity="activity value for bacteriostat". Slight activity indicates a difference of zero logarithm steps between the control and the sample, significant activity indicates a difference of more than 1 and strong activity indicates a difference of more than 3.

While the cotton and the untreated fibres according to Example 1 displayed no antibacterial effect, no more bacteria could be detected on the fibres treated with silver nitrate according to Example 4. This means that the fibres treated with silver showed a strong antibacterial effect.

In the following Table 6, the levels after 18 hours of incubation are specified for the standard cotton as a growth control and for a standard Lyocell fibre and the modified

TABLE 5

|  |  | Modified Lyocell fibre Example 2 | | Lyocell fibre Example 3 | |
| --- | --- | --- | --- | --- | --- |
|  |  | [mg/kg fibre] | [mmol/kg fibre] | [mg/kg fibre] | [mmol/kg fibre] |
| Example 4 | Silver | 1855 | 17.2 | 237 | 2.2 |
| Example 5 | Copper | 899 | 14.2 | 591 | 9.3 |
| Example 6 | Zinc | 756 | 11.6 | 526 | 8.0 |
| Example 7 | Mercury | 9460 | 47.2 | 376 | 1.9 |
| Example 8 | Tin | 1670 | 14.1 | 1030 | 8.7 |
| Example 9 | Cadmium | 1270 | 11.3 | 793 | 7.1 |
| Example 10 | Silver | 1410 | 13.1 | 207 | 1.9 |
| Example 11 | Arsenic | 170 | 2.3 | 72 | 1.0 |
| Example 12 | Lead | 2720 | 13.1 | 1790 | 8.6 |
| Example 13 | Antimony | 496 | 4.1 | 267 | 2.2 |

Lyocell fibre produced according to Example 1. Furthermore, the treated, modified Lyocell fibres produced according to Example 4 and a similarly treated standard Lyocell fibre are listed.

TABLE 6

|  | Staphylococcus aureus conc. after 18 hours [log CFU] | Klebsiella pneumoniae conc. after 18 h [log CFU] |
|---|---|---|
| Standard cotton | 5.62 | 7.38 |
| Lyocell fibre, untreated, Example 3 | 5.51 | 7.85 |
| Modified Lyocell fibre, untreated, Example 1 | 6.25 | 7.92 |
| Lyocell fibre, treated, similar to Example 4 | 0 | 0 |
| Modified Lyocell fibre, treated, similar to Example 4 | 0 | 0 |

EXAMPLE 16

In the manufacture of high-purity silver, an anode of raw silver is subjected to electrolytic refining in conventional Moebius cells. In this process, silver nitrate, as an electrolyte, is used at a concentration of 5-80 g/l of silver at a temperature of 40° C. While it is true that the electrolyte is constantly reused, nevertheless, during maintenance work and standstills, waste waters with silver concentrations that are also partially less than in the electrolyte do occur. The recovery of the silver nitrate by means of the Lyocell moulded body according to the invention was tested using a synthetic silver nitrate solution. 2 kg of fibre from Example 2 were filled into a 5 l PP pressure tank with backup plate. The fibre was subsequently moistened with 5 l of completely demineralised water. 10 l of silver nitrate, at a concentration of approximately 1 g Ag/l, were introduced into a PP container. Using a constricted tube pump, this quantity was pumped over the pressure tank (with the moistened fibres from Example 3) to recirculate. With the built-in rotameter, a recirculation flow rate of 30 l/h was selected.

A sample was drawn every 5 minutes in order to determine the Ag concentration. The following Table 7 presents the progression of the silver amount in the liquid phase.

It could be shown that practically all of the silver is absorbed from the fibre.

TABLE 7

| Time | Silver amount in the liquid phase [g] |
|---|---|
| 5 | 9.6 |
| 10 | 7.8 |
| 15 | 5.4 |
| 20 | 4.7 |
| 25 | 4.1 |
| 30 | 2.9 |
| 35 | 1.4 |
| 40 | 1.3 |
| 45 | 0.8 |
| 50 | 0.6 |
| 55 | 0.37 |
| 60 | 0.34 |
| 65 | 0.25 |
| 70 | 0.26 |
| 75 | 0.23 |

Figure 1:
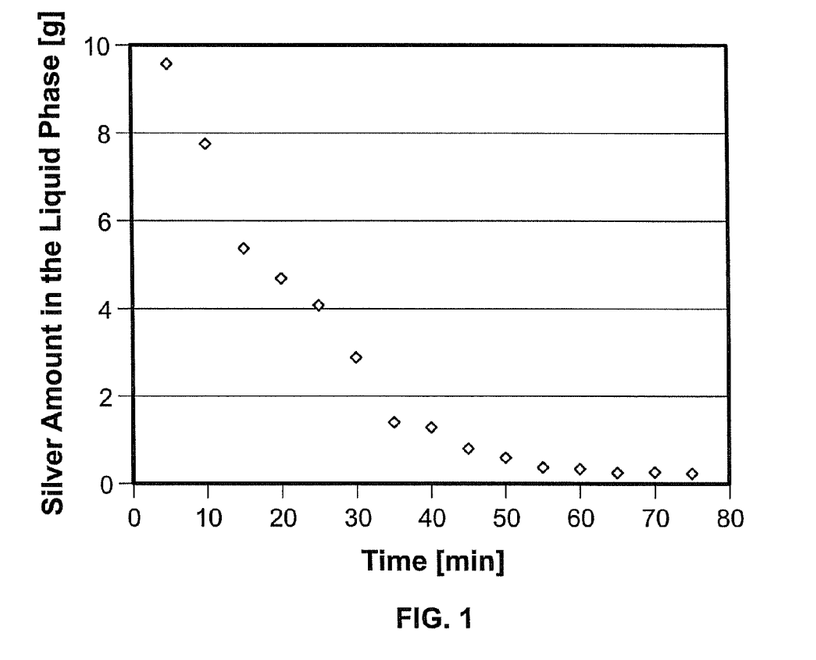

FIG. 1 is a graphic representation of the results obtained in this example.

EXAMPLE 17

To 30 g of a Lenzing modal fibre (titre fineness: 0.12 tex, from the company Lenzing AG) 1 l of 0.1 M $AgNO_3$ solution was added and shaken for four hours. The treatment took place analogously to Example 10.

After this treatment, the fibre material was filtered by suction and washed with completely demineralised water until no more silver traces (test with a NaCl solution) were detected.

The fibres were dried in a circulating air drying cabinet at approximately 105° C.

The fibre obtained in this way was analyzed for its silver content. For this purpose, to a portion of the fibre material 1 N nitric acid was added (1 hour) in order to dissolve the silver. The nitric acid solution was filtered off and then titrated with 0.1 N NaCl. To improve the visibility of the end point of the titration, the filtrate was heated so that the resulting precipitate agglomerated.

TABLE

|  |  | Modified modal fibre Example 17 [mg/kg fibre] |
|---|---|---|
| Example 17 | Silver | 351 |

EXAMPLE 18

The fibres produced according to Example 17 were then examined for bacterial resistance.

The determination took place analogously to Example 15.

The determination was carried out following the Japanese Industrial Standard, JIS L1902:1998 Testing method for antibacterial of textiles. *Staphylococcus aureus*, as a gram-positive bacterial strain, and *Klebsiella pneumoniae*, as a gram-negative bacterial strain, were used.

The bacteria were applied to fibre material from Example 17 and, as a growth control, standard cotton and cellulose were subjected to the same test treatment.

After 18 hours of incubation, the bacterial growth inhibiting or bacterial reduction activity is determined from the bacterial content (the number of colony-forming units—CFU) in the sample and the control.

To calculate this antibacterial activity, the difference is formed between the base-10 logarithms of the number of colony forming units (CFU) in the control sample and the sample, each after 18 hours of incubation.

The classification is done in three classes—slight activity, significant activity and strong activity="activity value for bacteriostat". Slight activity indicates a difference of zero logarithm steps between the control and the sample, significant activity indicates a difference of more than 1 and strong activity indicates a difference of more than 3.

While the cotton and the cellulose displayed no antibacterial effect, no more bacteria could be detected on the fibres treated with silver nitrate according to Example 17. This means that the fibres treated with silver showed a strong antibacterial effect.

In the following table, the levels after 18 hours of incubation are specified for the standard cotton and cellulose as a growth control and for a modified Lyocell fibre produced according to Example 17.

|  | *Staphylococcus aureus* conc. after 18 hours [log CFU] | *Klebsiella pneumoniae* conc. after 18 hours [log CFU] |
|---|---|---|
| Standard cotton | 3.32 | 7.52 |
| Standard cellulose | 5.80 | 7.54 |
| Modified modal fibre in accordance with Example 17 | 0 | 0 |

EXAMPLE 19

The washing out characteristics of a Lyocell fibre with algae incorporation (Example 2) treated according to Example 10 (with 0.1 M AgNO$_3$) was tested in the following way:

25 g of the dried fibre were prepared in a liter of completely demineralised water. The water was examined qualitatively after standing for 24 hours. After the sample was taken, the fibre material was squeezed out and supplied with new completely demineralised water. This process was repeated 4 times (a total of 4 phases of 24 hours each). The silver content of the fibre was determined before and after the test series. The data are summarized in the following Table.

EXAMPLE 20

The washing out characteristics of a Lyocell fibre (Example 3 treated according to Example 10 (with 0.1 M AgNO$_3$)) was tested in the same way as described in Example 19.

The data are summarized in the following Table.

EXAMPLE 21

The washing out characteristics of a Lenzing viscose modal fibre (titre fineness: 0.12 tex, from the Lenzing AG company) was treated according to Example 17 (with 0.1 M AgNO$_3$) and tested in the same way as described in Example 19.

The data are summarized in the following Table.

| | Silver content of the fibre [mg/kg fibre] | | | | |
|---|---|---|---|---|---|
| Time | At the start | After the 1$^{st}$ phase (24 h) | After the 2$^{nd}$ phase (24 h) | After the 3$^{rd}$ phase (24 h) | After the 4$^{th}$ phase (24 h) |
| Example 19 - modified Lyocell with algae incorporation | 1842 | 1605 | 1427 | 1278 | 1191 |

| | Silver content of the fibre [mg/kg fibre] | | Qualitative silver detection in completely demineralised water for each washing phase | | | |
|---|---|---|---|---|---|---|
| | | | 1$^{st}$ phase | 2$^{nd}$ phase | 3$^{rd}$ phase | 4$^{th}$ phase |
| Time | At the start | After the end | (24 h) | (24 h) | (24 h) | (24 h) |
| Example 19 - modified Lyocell with algae incorporation | 1842 | 1191 | Pos. | Pos. | Pos. | Pos. |
| Example 20 - modified Lyocell without algae incorporation | 216 | 63 | Pos. | Pos. | Pos. | Pos. |
| Example 21 - modified viscose modal with algae incorporation | 351 | 111 | Pos. | Pos. | Pos. | Pos. |

EXAMPLE 22

Fibre loaded with silver, from Example 10, was mixed with normal Lyocell fibre from Example 3, so that an Ag concentration of approximately 100 mg of Ag/kg fibre was present in the mixture.

A card sliver was produced from this mixture for homogenization purposes, and this card sliver was examined for antibacterial properties according to Example 18. In the following table, the levels after 18 hours of incubation are specified for the standard cotton and cellulose as a growth control and for the modified Lyocell fibre produced according to Example 22.

EXAMPLE 23

Fibre loaded with silver, from Example 10, was mixed with normal Lyocell fibre from Example 3, so that an Ag concentration of approximately 50 mg Ag/kg fibre was present in the mixture.

A card sliver was produced from this mixture for homogenization purposes, and this card sliver was examined for antibacterial properties according to Example 18. In the following table, the levels after 18 hours of incubation are specified for the standard cotton and cellulose as a growth control and for the modified Lyocell fibre produced according to Example 22.

EXAMPLE 24

Fibre loaded with silver, from Example 10, was mixed with normal Lyocell fibre from Example 3, so that an Ag concentration of approximately 5 mg Ag/kg fibre was present in the mixture.

A card sliver was produced from this mixture for homogenization purposes, and this card sliver was examined for antibacterial properties according to Example 18. In the following table, the levels after 18 hours of incubation are specified for the standard cotton and cellulose as a growth control and for the modified Lyocell fibre produced according to Example 22.

|  | Staphylococcus aureus conc. after 18 h [log CFU] | Klebsiella pneumoniae conc. after 18 hours [log CFU] |
| --- | --- | --- |
| Standard cotton | 3.32 | 7.52 |
| Standard cellulose | 5.80 | 7.54 |
| Card sliver with approx. 100 mg Ag/kg fibre - Example 22 | 0 | 0 |
| Card sliver with approx. 50 mg Ag/kg fibre - Example 23 | 0 | 0 |
| Card sliver with approx. 5 mg Ag/kg fibre - Example 24 | 0 | 0 |

EXAMPLE 25

3210 g NMMNO (60.5%), 321 g MoDo, DP 500, solid content 94%, 2.0 g propyl gallate (~0.63% referred to the cellulose content) as well as 26 g of the brown algae *Ascophyllum nodosum* (broken into small pieces) and 20 mg silver (I) oxide (broken into small pieces—max. size 1.5 μm—supplier: Sigma Aldrich, Product Number 10228) were mixed and the mixture obtained in this way was heated to 94° C. A discontinuously produced spinning solution with a cellulose content of approximately 11.8%, a solids content of 12.7% and a viscosity of 5,264 Pa.s was obtained. The spinning solution obtained in this way was spun into fibres, whereby the following spinning conditions were maintained:

| | |
| --- | --- |
| Storage tank temperature = | 90° C. |
| Spin block temperature, nozzle = | 80° C. |
| Spinning bath = | 4° C. |
| Spinning bath concentration (starting) = | 0% (distilled water) |
| Spinning bath concentration (end) = | 5% NMMNO |
| Spinning pump = | 0.6 cm$^3$/r |
| Nozzle filter = | 19200 M/cm$^2$ |
| Spinning nozzle = | 500 hole 90 μm; Au/Pt |
| Final take-off = | 30 m/min |

The fibres were cut to a fibre staple of 40 mm, washed without solvent and given a 10 g/l softening (50% Leomin OR-50% Leomin WG (fatty acid polyglycol ester containing nitrogen, from the company Clariant GmbH)) at 45° C. or the fat overlay was applied for improved further processing of the fibre and dried at 105° C.

After the drying, fibre moisture of 11% was regulated. No additional bleaching process was carried out before the drying.

EXAMPLE 26

A cellulose xanthate was produced from a mixture of 33% cellulose by weight, 17% caustic soda solution by weight and 50% water by weight by adding 32% carbon disulfide referred to the cellulose. Following this, the xanthate was converted to a spinning solution with 6% cellulose by weight, 6% NaOH by weight and essentially water and reaction products by adding diluted caustic soda solution subsequent to the xanthate production by 2 hours of stirring.

EXAMPLE 27

60 g of sodium sulphate (Glauber's salt) as a poreforming agent and 5 g of viscose short cut fibres (Svenska Rayon Company, Swelan type with 1.0 dtex, 5 mm) were added to 1.5 kg of the viscose solution obtained from Example 26 and intensively stirred.

The mass was filled into a perforated form and placed for 30 minutes into a first precipitation bath that was at a temperature of 95° C. and that contained 10 g/l of sodium carbonate and 80 g/l of sodium sulphate.

Subsequently, the pre-precipitated mass was transferred to a second bath for 15 minutes; this bath's temperature was 60° C. and it contained 70 g/l sulphuric acid and 140 g/l sodium sulphate, in order to completely regenerate the cellulose.

Then the sponge was washed, squeezed out and dried.

EXAMPLE 28

The sponge is produced analogously to Example 27, whereby an additional 8 g of brown algae powder, finely reduced to small pieces, was added to the viscose solution.

The dried and desulphurised sponge was then transferred to a bath of 0.1 N silver nitrate and left in the bath for approximately 1 hour. The sponge containing Ag was then washed free and dried again.

Like all other manufactured sponges, the sponge was examined for antibacterial properties.

The determination was carried out following the Japanese Industrial Standard, JIS L1902:1998 Testing method for antibacterial of textiles. *Staphylococcus aureus*, as a grampositive bacterial strain, and *Klebsiella pneumoniae*, as a gram-negative bacterial strain, were used.

The bacteria were applied to the sponge and, as a growth control, the standard sponge from Example 27 was subjected to the same test treatment.

After 18 hours of incubation, the bacterial growth inhibiting or bacterial reduction activity is determined from the bacterial content (the number of colony-forming units—CFU) from the sample and the control.

While the standard sponge from Example 27 displayed no antibacterial effect, no more bacteria were detected on the sponge from Example 28. This means that the sponge with incorporated brown algae and treated with silver displays a strong antibacterial effect because of the attachment of the silver ions to the incorporated brown algae material.

EXAMPLE 29

A sponge was produced analogously to Example 27. There was, however, no addition of algae powder and no addition of viscose short cut fibres; instead, 35 g of a short cut Lyocell fibre with incorporated algae (12% algae referred to the cellulose—produced according to WO 01/62844) was added. A sponge was produced analogously to Example 28 and treated with silver nitrate.

This sponge also displayed a strong antibacterial effect.

Carbamate Sponges

EXAMPLE 30

To produce cellulose carbamate, first an alkali cellulose was produced from the chemical cellulose Borregaard SVS. The caustic soda solution was washed out of the processed alkali cellulose (35% cellulose by weight; 15% NaOH by weight; 50% water by weight) with water. After the cellulose (70% water by weight) activated in this way was squeezed out, 10 kg of the squeezed activated cellulose were mixed with carbamide (1.5 kg) in a kneading machine. In this process, the carbamide present in the water in the cellulose dissolved and was uniformly distributed in the cellulose.

This cellulose pulp was transferred to a reactor, which was equipped with a mixer and reflux cooler, and which already contained o-xylene (35 kg). The reactor contents were then heated to 145° C. for approximately 2 hours and then filtered off.

The residue obtained in this way was fed back into the reactor, in which approximately 25 kg of water had been placed. The xylene that was still adhering to the carbamate was stripped off at 88° C. After the filtration, the carbamate was washed out with hot (50° C.) and cold water. Then the carbamate was squeezed out. The produced carbamate displayed a nitrogen content of 2.6% (corresponds to a DS of 0.3) and a DP of 270.

EXAMPLE 31

Approximately 0.7 kg of strong solution were produced from 0.2 kg of the carbamate produced in Example 30, along with 0.22 kg caustic soda solution (30% by weight), 0.26 kg water and 10 g of brown algae powder, finely broken down, type *Ascophyllum nodosum*. All reactants were pre-cooled and the reaction itself took place at a temperature of 0° C. (Composition of the strong lye: 11.0% cellulose by weight, 9.5% NaOH by weight.) To the cooled strong solution 65 g of sodium sulphate as a pore-forming agent, 25 g of acid sodium carbonate as a blowing agent, 30 g of viscose short cut fibres (Svenska Rayon Company, Swelan type with 1.0 dtex, 5 mm) and 0.2 kg of cooled caustic soda solution (1%) were added and intensively stirred.

The mixture was transferred into a larger vacuum container and kept at 100° C. for approximately 20 minutes. The decomposition gases were taken away via applied vacuum.

The foamed mass was placed into a warm bath, approximately 40° C., made of sulphuric acid (70 g/l) and sodium sulphate (140 g/l), for 10 minutes in order to precipitate the cellulose and fix the structure. After a washing step in completely demineralised water, the sponge was kept in a hot decomposition bath (85° C.) of caustic soda solution (20 g/l) and sodium sulphate (100 g/l) for 10 minutes. Then the sponge was washed, squeezed out and dried.

The neutrally washed and dried sponge was then transferred to a bath of 0.1 N silver nitrate and left in the bath for approximately 1 hour. The sponge containing Ag was then washed free and dried again.

The carbamate sponge displayed a strong antibacterial effect.

EXAMPLE 32

A sponge was produced analogously to Example 31, but there was no addition of algae powder; instead, approximately 11 g of treated algae powder was added.

The powder was treated in the following way: approximately 25 g of algae powder, finely broken down, was treated for 1 hour with 1 l of 0.1 N silver nitrate solution. The treated powder was centrifuged off and washed with water, then dried in a further step.

This sponge also displayed a strong antibacterial effect.

EXAMPLE 33

A sponge was produced analogously to Example 31. There was, however, no addition of algae powder during the production of the strong solution. Furthermore, no viscose short cut fibres were added; instead, 45 g of a short cut Lyocell fibre with incorporated algae was added (12% algae referred to cellulose—produced according to WO 01/62844).

A sponge was produced analogously to Example 31 and treated with silver nitrate.

This sponge also displayed a strong antibacterial effect.

EXAMPLE 34

A sponge was produced analogously to Example 33. There was, however, an addition of a short cut Lyocell fibre (treated with silver nitrate) with incorporated algae (12% algae referred to cellulose—produced according to WO 01/62844). The fibre was treated in the following way: approximately 100 g of fibre were treated for 1 hour with 3 l of 0.1 N silver nitrate solution. The fibre was filtered off, washed with water and subsequently dried.

A sponge was produced analogously to Example 33, but not treated with silver nitrate.

The sponge produced in this way displayed a strong antibacterial effect.

Lyocell Sponges

EXAMPLE 35

2967 g NMMNO (49.8%), 302 g MoDo, DP 500, dry content 94%, 1.8 g propyl gallate (0.63% referred to the cellulose content) and 23 g of brown algae powder, finely broken down (approximately 8% referred to the cellulose content), type *Ascophyllum nodosum* were mixed and the mixture obtained in this way was heated to 94° C. A discontinuously produced spinning solution with a cellulose content of 14.2% was obtained.

In a heated kneading machine (IKA-Werke HKS 10), 1550 g of NMMO monohydrate (86%) were dissolved by heating and mixed with 1450 g of N,N-dimethylformamide (DMF), an organic solvent, in order to prepare or adjust the viscosity for mixing in the reinforcing fibres. This measure was the first to solve the problem of the high viscosities predominant in the amine oxide-cellulose-water system for sponge manufacture (U.S. Pat. No. 4,196,282).

Then 30 g of viscose short cut fibres (Svenska Rayon Company, Swelan type with 1.0 dtex, 5 mm) and a pore-forming agent (90 g $Na_2SO_4$) were stirred into this mixture. Where necessary, a blowing agent can also be added.

This mixture is then added to the spinning solution produced. N,N-dimethylformamide, with a boiling point of 153° C., was evaporated under vacuum (80 mbar), so that a homogenous cellulose solution, reinforced with fibre and with a cellulose concentration of approximately 8%, was regulated. It was observed that the cellulosic short cut fibres swell during the distillation of the DMF, but do not completely become a solution, so that the sponge reinforcement effect is still maintained after being shaped into the corresponding moulded product.

The mass is then filled into a perforated form, approximately 7 mm high, and placed into a 50° C. precipitation bath mixture for 20 minutes.

The sponge goes through an additional 4 washing baths every 15 minutes to wash the solvent free; each bath contains completely demineralised water at a temperature of 30° C. Then the sponge is squeezed out and dried in a drying cabinet at 90° C. for approximately 2 hours.

Where necessary, a softening substance can be added to the sponge in order to compensate for the brittleness.

The dried sponge was then transferred to a bath of 0.1 N silver nitrate and left in the bath for approximately 1 hour. The sponge containing Ag was then washed free and dried again.

The sponge treated with silver also displays a strong antibacterial effect.

EXAMPLE 36

A sponge was produced analogously to Example 35, but there was no addition of algae powder during the production of the solution; instead, approximately 25 g of treated algae powder was added along with the addition of the pore-forming agent and short cut fibres.

The powder was treated in the following way: approximately 25 g of algae powder, finely broken down, was treated for 1 hour with 1 l of 0.1 N silver nitrate solution. The treated powder was centrifuged off and washed with water, then dried in a further step.

A sponge was produced analogously to Example 35, but not treated with silver nitrate.

This sponge also displayed good rigidity and a strong antibacterial effect.

EXAMPLE 37

A sponge was produced analogously to Example 35. There was, however, no addition of algae powder during the production of the solution. Furthermore, no Lyocell short cut fibres were added; instead, three times as much Lyocell fibre with incorporated algae (12% algae referred to the cellulose—produced according to WO 01/62844) was added. A sponge was produced analogously to Example 35 and treated with silver nitrate.

In spite of the reduced amount of incorporated algae, this sponge also displayed a strong antibacterial effect.

EXAMPLE 38

A sponge was produced analogously to Example 37. There was, however, an addition of a short cut Lyocell fibre (treated with silver nitrate) with incorporated algae (12% algae referred to cellulose—produced according to WO 01/62844). The fibre was treated in the following way: approximately 100 g of fibre were treated for 1 hour with 3 l of 0.1 N silver nitrate solution. The fibre was filtered off, washed with water and subsequently dried in a further step.

A sponge was produced analogously to Example 37, but not treated with silver nitrate.

This sponge also displayed a strong antibacterial effect.

Information on the Assessment of the Antibacterial Effect:

The determination was carried out following the Japanese Industrial Standard, JIS L1902:1998 Testing method for antibacterial of textiles. *Staphylococcus aureus*, as a gram-positive bacterial strain, and *Klebsiella pneumoniae*, as a gram-negative bacterial strain, were used.

The bacteria were applied to the sponge and, as a growth control, cellulose was subjected to the same test treatment.

After 18 hours of incubation, the bacterial growth inhibiting or bacterial reduction activity is determined from the bacterial content (the number of colony-forming units—CFU) in the sample and the control.

To calculate this antibacterial activity, the difference is formed between the base-10 logarithms of the number of colony forming units (CFU) in the control sample and the sample, each after 18 hours of incubation.

The classification is done in three classes—slight activity, significant activity and strong activity="activity value for bacteriostat". Slight activity indicates a difference of zero logarithm steps between the control and the sample, significant activity indicates a difference of more than 1 and strong activity indicates a difference of more than 3. The difference in the logarithm steps is also called the specific efficacy.

The bacteria were applied to the sponge and, as a growth control, the standard sponge from Example 27 was subjected to the same test treatment.

After 18 hours of incubation, the bacterial growth inhibiting or bacterial reduction activity is determined from the bacterial content (the number of colony-forming units—CFU) in the sample and the control.

While the standard cotton that was also measured as the control showed no antibacterial effect, a strong antibacterial effect was detected in the sponges from Examples 3-13, as shown in the following table.

|  | Specific efficacy | | Antibacterial effect |
| --- | --- | --- | --- |
|  | *Staphylococcus aureus* | *Klebsiella pneumoniae* | [slight, significant, strong] |
| Standard cotton | +2.09 | −2.05 | slight |
| Example 28 (viscose) | +5.51 | +7.85 | strong |
| Example 29 (viscose) | +5.51 | +7.85 | strong |
| Example 31 | +5.51 | +7.85 | strong |

-continued

| | Specific efficacy | | Antibacterial effect |
|---|---|---|---|
| | Staphylococcus aureus | Klebsiella pneumoniae | [slight, significant, strong] |
| Example 32 (carbamate) | +5.01 | +6.31 | strong |
| Example 33 (carbamate) | +5.51 | +7.85 | strong |
| Example 34 (carbamate) | +4.65 | +5.64 | strong |
| Example 35 (Lyocell) | +5.51 | +7.85 | strong |
| Example 36 (Lyocell) | +5.21 | +6.88 | strong |
| Example 37 (Lyocell) | +5.51 | +7.85 | strong |
| Example 38 (Lyocell) | +5.01 | +6.45 | strong |

The sponges according to the invention display the following advantages:

- A necessary insolubility of the added bactericidal substances in water, alkalis and acids in temperature ranges from 20-100° C.
- A necessary chemical stability in the face of strong lyes and strong acids and diverse oxidants.
- Good miscibility of the substance with the bactericidal effect with the cellulose solution to be formed without negatively influencing the spinning process and shaping process, because it is introduced indirectly via a biological carrier material, and not directly.
- The diffusion effect of the substances with a bactericidal effect in the direction of the fibre surface is, naturally, proven for biological substances such as cellulose and algae.
- Good ecological and toxicological compatibility of the substance with the bactericidal effect because, on the one hand, no organic chlorine compounds are used and, on the other hand, the bactericide is only released in connection with moisture.

The invention claimed is:

1. A method for removing heavy metals from media containing heavy metals, comprising bringing the medium containing heavy metals into contact with a Lyocell moulded body, wherein the Lyocell moulded body comprises an algae material.

2. The method according to claim 1, wherein the Lyocell moulded body is an ion exchanger or filtering material.

3. The method according to claim 1, wherein the medium containing heavy metals is an aqueous solution or a gas.

4. The method according to claim 1, wherein the heavy metals are selected from the group consisting of Ag, Cu, Zn, Hg, Sn, Cd, As, Pb, Sb, Zr, Ni, Fe, Au, Pd, Pt, Ir and mixtures thereof in metallic, ionic and/or complexed form.

5. The method according to claim 1, wherein the Lyocell moulded body is in the form of fibres, filaments, fibrous webs, foils, films, membranes, non-wovens, filters, cigarette filters and/or filter papers.

6. A cellulosic moulded body, comprising at least one heavy metal adsorbed on it, wherein the cellulosic moulded body comprises an algae material.

7. The cellulosic moulded body according to claim 6, wherein the cellulosic moulded body is selected from the group consisting of carbamate, viscose and Lyocell moulded bodies.

8. The cellulosic moulded body according to claim 6, wherein the content of the at least one heavy metal is at least roughly 5 mg/kg, relative to the total weight of the cellulosic moulded body.

9. The cellulosic moulded body according to claim 6, wherein the at least one heavy metal is selected from the group consisting of Ag, Cu, Zn, Hg, Sn, Cd, As, Pb, Sb, Zr, Ni, Fe, Au, Pd, Pt, Ir and mixtures thereof in metallic, ionic and/or complexed form.

10. The cellulosic moulded body according to claim 9, wherein the at least one heavy metal is selected from the group consisting of Ag, Cu, Zn, Zr, Au and mixtures thereof in metallic, ionic and/or complexed form.

11. The cellulosic moulded body according to claim 6, wherein the cellulosic moulded body is in the form of fibres, filaments, fibrous webs, foils, films, membranes, non-wovens, cigarette filters and/or filters.

12. The cellulosic moulded body according to claim 6, further comprising a natural or synthetic polymer.

13. The cellulosic moulded body according to claim 12, wherein the natural or synthetic polymer is selected from the group consisting of polyester, polyamide, polyvinyl chloride, cellulose carbamate, cupro, viscose, polyacrylonitrile, polyolefin, Teflon, hemp, wool, linen and cotton.

14. An antibacterial fibre, comprising a cellulosic moulded body according to claim 6.

15. An antibacterial fibrous web, comprising a cellulosic moulded body according to claim 6.

16. An antibacterial membrane, comprising a cellulosic moulded body according to claim 6.

17. An antibacterial sausage casing, comprising a cellulosic moulded body according to claim 6.

18. A hygiene article, comprising a cellulosic moulded body according to claim .

19. Products with medical applications, comprising a cellulosic moulded body according to claim 6.

20. Sterile protective clothing, comprising a cellulosic moulded body according to claim 6.

21. An antibacterial water filter, comprising a cellulosic moulded body according to claim 6.

22. An antibacterial sponge, comprising a cellulosic moulded body according to claim 6.

23. A cigarette filter, comprising a cellulosic moulded body according to claim 6.

* * * * *